(12) United States Patent
Iino et al.

(10) Patent No.: US 10,113,143 B2
(45) Date of Patent: Oct. 30, 2018

(54) CELL CULTURE BAG AND METHOD FOR MANUFACTURING CELL CULTURE BAG

(71) Applicant: YOKOGAWA ELECTRIC CORPORATION, Musashino-shi, Tokyo (JP)

(72) Inventors: Toshio Iino, Tokyo (JP); Tango Hioki, Tokyo (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 157 days.

(21) Appl. No.: 14/709,553

(22) Filed: May 12, 2015

(65) Prior Publication Data

US 2015/0344829 A1 Dec. 3, 2015

(30) Foreign Application Priority Data

May 29, 2014 (JP) ................. 2014-111151

(51) Int. Cl.
C12M 1/00 (2006.01)
C12M 1/34 (2006.01)

(52) U.S. Cl.
CPC ............ *C12M 23/14* (2013.01); *C12M 29/04* (2013.01); *C12M 41/00* (2013.01); *C12M 41/34* (2013.01)

(58) Field of Classification Search
CPC ...... C12M 23/14; C12M 29/04; C12M 41/00; C12M 41/34
USPC ...................................... 435/287.9
See application file for complete search history.

(56) References Cited

U.S. PATENT DOCUMENTS

| | | | |
|---|---|---|---|
| 4,945,060 A | 7/1990 | Turner et al. | |
| 5,217,875 A | 6/1993 | Karpf et al. | |
| 2005/0163667 A1* | 7/2005 | Krause | B01L 3/505 422/400 |
| 2005/0239198 A1 | 10/2005 | Kunas et al. | |
| 2008/0202490 A1* | 8/2008 | Dodo | A61F 7/034 126/263.07 |
| 2009/0242173 A1 | 10/2009 | Mitchell et al. | |
| 2010/0129899 A1 | 5/2010 | Oosterhuis et al. | |
| 2012/0055791 A1* | 3/2012 | Leonard | G01N 27/4167 204/433 |
| 2012/0171760 A1 | 7/2012 | Rao et al. | |
| 2012/0238011 A1 | 9/2012 | Tuohey et al. | |

FOREIGN PATENT DOCUMENTS

| | | |
|---|---|---|
| JP | 0216965 A | 1/1990 |
| JP | 04-500307 A | 1/1992 |
| JP | 04-505256 A | 9/1992 |
| JP | 5508556 A | 12/1993 |
| JP | 2628406 B2 | 7/1997 |
| JP | 3109740 B2 | 11/2000 |
| JP | 2007534335 A | 11/2007 |
| JP | 2009-222429 A | 10/2009 |
| JP | 2010-136628 A | 6/2010 |

(Continued)

*Primary Examiner* — Michael L Hobbs
(74) *Attorney, Agent, or Firm* — Sughrue Mion, PLLC (57) ABSTRACT

A cell culture bag is provided. The cell culture bag includes: an external film of the cell culture bag; at least one sensor chip arranged on a culture fluid side of the external film, the at least one sensor chip including a layer reacting to an object to be detected; and a permeable film that covers a culture fluid side of the sensor chip, the permeable film permeating the object to be detected.

4 Claims, 13 Drawing Sheets

(56) References Cited

FOREIGN PATENT DOCUMENTS

| JP | 2010529854 A | 9/2010 |
|---|---|---|
| JP | 2013502930 A | 1/2013 |
| WO | 90/13663 A1 | 11/1990 |
| WO | 90/14414 A1 | 11/1990 |
| WO | 9219764 A1 | 11/1992 |

* cited by examiner

CELL CULTURE BAG AND METHOD FOR MANUFACTURING CELL CULTURE BAG

CROSS-REFERENCE TO RELATED APPLICATION

This application claims priority from Japanese Patent Application No. 2014-111151 filed with the Japan Patent Office on May 29, 2014, the entire content of which is hereby incorporated by reference.

BACKGROUND

1. Technical Field

This disclosure relates to a cell culture bag and a method for manufacturing the cell culture bag.

2. Related Art

In a cell culture process for manufacturing, for example, medicines, to maintain conditions optimal to cultivating cells, such as a dissolved oxygen concentration in a culture fluid, pH, a nutrient component concentration, and a culture fluid temperature, measuring these values is important.

As a culture container for cell culture, flasks had been generally used. However, recently, single-use cell culture bags have been widely used. The cell culture bags are commercially available in a state of being sterilized. These cell culture bags feature a simple handling, high permeability to gas, allowing high density culture with good efficiency, or a similar property.

Figure 12:
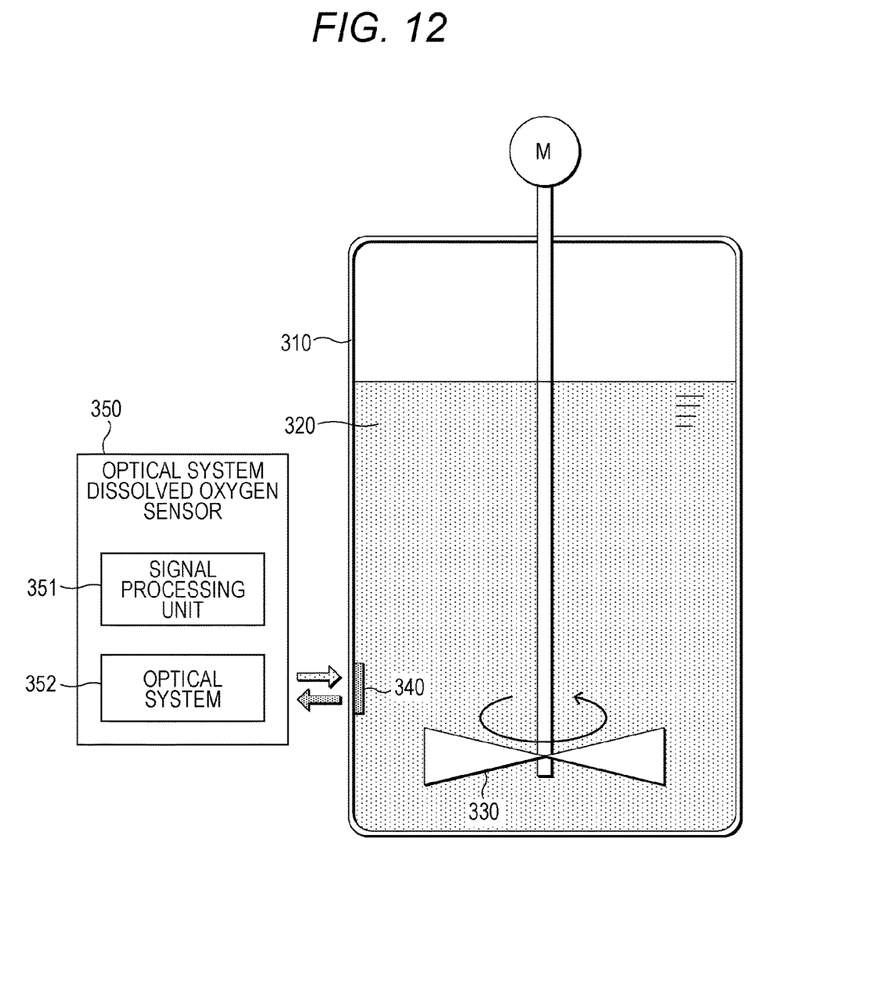
FIG. 12 is an explanatory view of a conventional measurement of dissolved oxygen concentration targeting a culture fluid in the cell culture bag.

The following describes a measurement of the culture fluid in the cell culture bag with the measurement of the dissolved oxygen concentration as an example with reference to FIG. 12. As a dissolved oxygen concentration sensor, some methods such as an electrode method, a method for using a reagent, and an optical method have been put to practical use. Here, a dissolved oxygen sensor of the optical method has been used.

To optically measure the dissolved oxygen concentration, an oxygen detection sensor chip containing a substance reacting to oxygen is arranged in the culture fluid. Then, excitation light is irradiated to the sensor chip. A phosphorescence emitted from the sensor chip at this moment is observed. The higher dissolved oxygen concentration delays a phase of the phosphorescence more than a phase of the excitation light, and the strength of the phosphorescence reduces. Therefore, modulating the excitation light to be irradiated with, for example, sine wave, allows measuring the phase delay or the strength of the phosphorescence to be observed. Thus, the dissolved oxygen concentration in the culture fluid can be obtained.

In the drawing, a cell culture bag 310 houses a culture fluid 320 which is a culture medium. The cell culture bag 310 uses a stirring blade 330 to uniform an oxygen concentration distribution or a similar distribution in the culture fluid 320. A motor rotates the stirring blade 330 at a predetermined rotation speed.

To the inside of the cell culture bag 310, an oxygen detection sensor chip 340 is attached. An optical system dissolved oxygen sensor 350 includes a signal processing unit 351 and an optical system 352. The optical system 352 includes an excitation optical system and a receiving optical system. The excitation optical system irradiates the excitation light modulated with, for example, the sine wave on the sensor chip 340. The receiving optical system receives the phosphorescence emitted by the sensor chip 340 and converts the phosphorescence into an electrical signal. The signal processing unit 351 performs a predetermined signal process on the electrical signal which is obtained from the receiving optical system. This converts the received phosphorescence into the electrical signal corresponding to an oxygen concentration.

Figure 13:
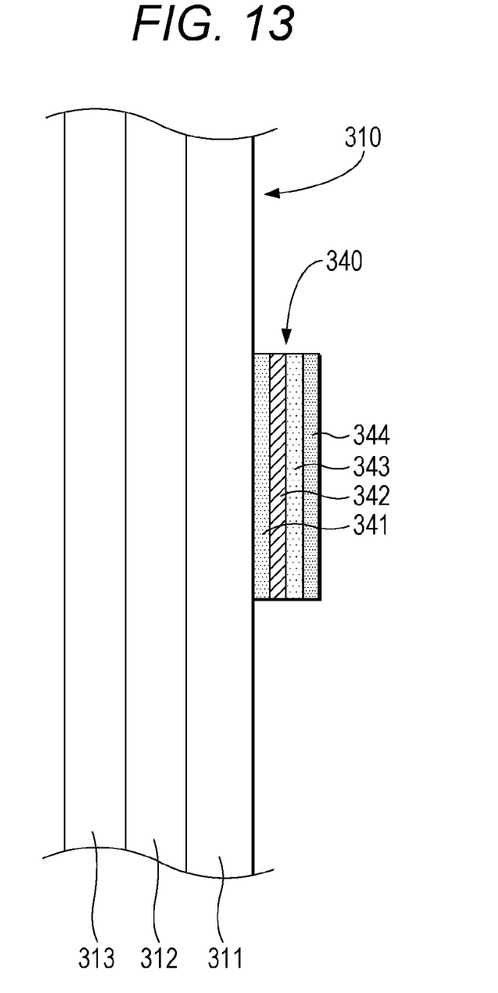
FIG. 13 illustrates a conventional exemplary constitution of the cell culture bag near a position where the sensor chip is attached and the sensor chip.

FIG. 13 illustrates an exemplary constitution of the cell culture bag 310 near a position where the sensor chip 340 is attached and the sensor chip 340. As illustrated in the drawing, the cell culture bag 310 has a laminated structure. For example, the cell culture bag 310 is constituted so as to be laminated in an order of an ethylene vinyl acetate (EVA) layer 311, an ethyl vinyl alcohol (EVOH) layer 312, and a low-density polyethylene (LDPE) layer 313 from the inside.

The sensor chip 340 includes a reflective film 343 and a light shielding film 344 arranged on one surface of an oxygen-sensitive film 342. The sensor chip 340 is attached to the cell culture bag 310 with an adhesive layer 341. The adhesive layer 341 is formed at the other surface of the oxygen-sensitive film 342.

The oxygen-sensitive film 342 is a photo-excited substance having, for example, oxygen quenching properties. As such photo-excited substance, a metalloporphyrin complex or a similar complex can be used. The reflective film 343 is used to reflect the excitation light to return this excitation light to the oxygen-sensitive film 342. Thus, the excitation light can be effectively utilized. The light shielding film 344 is used to prevent unwanted external light from entering the optical system 352.

Documents that disclose the related arts regarding the cell culture bag are, for example, JP-A-2009-222429, JP-A-2010-136628, Japanese Patent No. 2628406, Japanese Patent No. 3109740, and U.S. Pat. No. 2,012,171,760 descriptions.

SUMMARY

A cell culture bag according to an embodiment of the present disclosure includes: an external film of the cell culture bag; at least one sensor chip arranged on a culture fluid side of the external film, the at least one sensor chip including a layer reacting to an object to be detected; and a permeable film that covers a culture fluid side of the sensor chip, the permeable film permeating the object to be detected.

DESCRIPTION OF THE EMBODIMENTS

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

To culture cells, a tool directly in contact with the cells or a similar tool needs to be in an aseptic condition. Generally, a user attaches the sensor chip 340 separately purchased to the inside of the sterilized cell culture bag 310 for use. Accordingly, the user himself/herself needs to perform a sterilization treatment on the cell culture bag 310 after being attached using, for example, gamma rays. This compels the user to bear an excessive load. Additionally, this possibly results in insufficient sterilization treatment due to a shortage of skills, mishandling, or a similar cause.

The sensor chip 340 is exposed to the inside of the cell culture bag 310. Accordingly, the sensor chip 340 is used in a state of being in contact with the culture fluid. Accordingly, in the case of insufficient sterilization treatment, if a substance contained in the sensor chip 340 is eluted in the culture fluid, this may adversely affect the culture of the cells.

Therefore, an object of this disclosure is to provide a cell culture bag with a sensor chip not in contact with a culture fluid and reacting to a detection-target substance and a method for manufacturing this cell culture bag.

In order to solve the problem, a cell culture bag of this disclosure includes: an external film; at least one sensor chip arranged on a culture fluid side of the external film, the at least one sensor chip including a layer reacting to an object to be detected; and a permeable film that covers a culture fluid side of the sensor chip, the permeable film permeating the object to be detected.

The permeable film may cover an entire inner surface of the external film. Or, the permeable film may cover a part of a region including the sensor chip on the inner surface of the external film.

Moreover, the cell culture bag may include a plurality of the sensor chips arranged, the plurality of the sensor chips being different in size, and among the plurality of the sensor chips, a sensor chip having a largest size being arranged at a center.

In order to solve the problem, a method for manufacturing a cell culture bag of this disclosure includes: attaching at least one sensor chip including a layer reacting to an object to be detected to a roll material that becomes an external film; stacking a roll material that becomes a permeable film to the roll material that becomes the external film to cover the at least one sensor chip with the roll material that becomes the permeable film, the roll material that becomes the permeable film permeating the object to be detected; and performing thermocompression bonding on both the roll materials.

This disclosure provides the cell culture bag with the sensor chip reacting to the detection-target substance in the culture fluid and not in contact with this culture fluid, and the method for manufacturing this cell culture bag.

Figure 1:
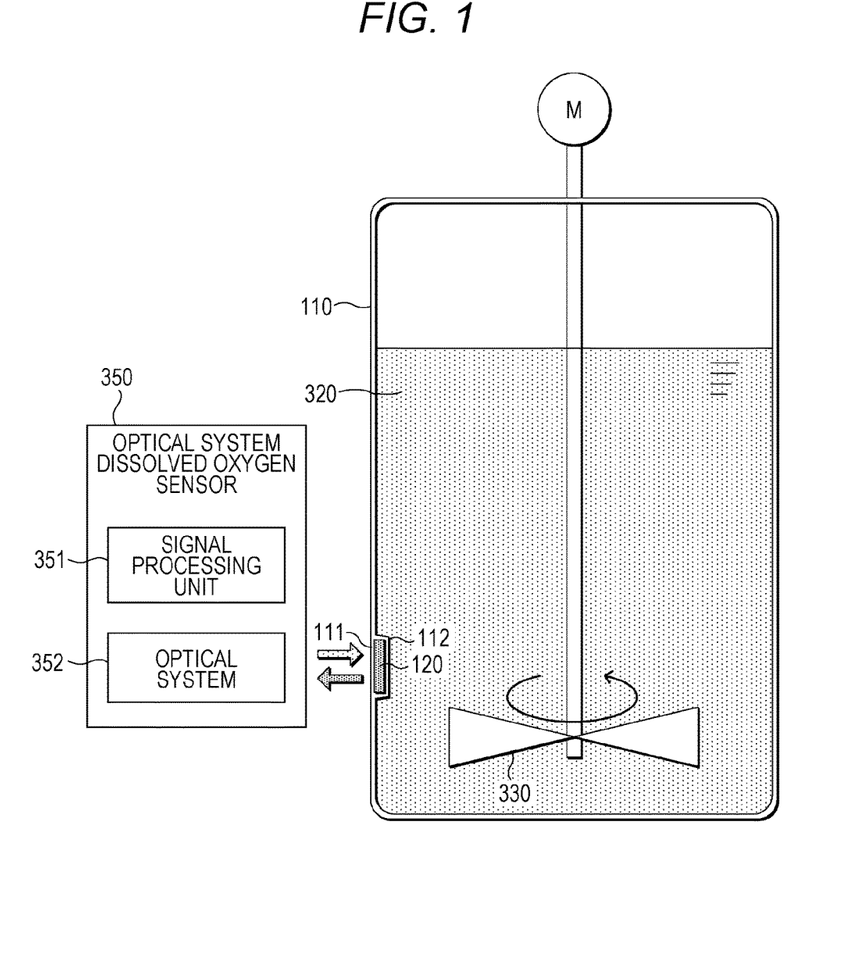
FIG. 1 is an explanatory drawing illustrating a use form of a cell culture bag according to an embodiment.

The embodiment of this disclosure will be described with reference to the accompanying drawings. FIG. 1 is an explanatory drawing illustrating a use form of a cell culture bag 110 according to an embodiment. In FIG. 1, like reference numerals designate corresponding or identical elements to the conventional cell culture bag.

The cell culture bag 110 houses the culture fluid 320 which is a culture medium. The cell culture bag 110 uses the stirring blade 330 to uniform an oxygen concentration distribution or a similar distribution in the culture fluid 320. A motor rotates the stirring blade 330 at a predetermined rotation speed. In the cell culture bag 110, a sparger that aerates the culture fluid 320 may be installed.

The cell culture bag 110 of this embodiment has a multilayer structure. At the innermost side layer of the cell culture bag 110, an oxygen permeable film 112 is formed. At the outside of the oxygen permeable film 112, an oxygen detection sensor chip 120 is arranged. In view of this, the sensor chip 120 is in contact with the culture fluid 320 via the oxygen permeable film 112. At the outermost side of the cell culture bag 110, an external film 111 is disposed. This allows employing the identical constitution to the conventional cell culture bag 310.

That is, the cell culture bag 110 of this embodiment has a structure that the oxygen permeable film 112 covers the sensor chip 120 arranged on the external film 111. Oxygen in the culture fluid 320 passes through the oxygen permeable film 112 and then reaches the sensor chip 120.

The optical system dissolved oxygen sensor 350 includes the signal processing unit 351 and the optical system 352. The optical system 352 includes the excitation optical system and the receiving optical system. The excitation optical system irradiates the excitation light modulated with, for example, the sine wave on the sensor chip 120. The receiving optical system receives the phosphorescence emitted by the sensor chip 120 and converts the phosphorescence into an electrical signal. The signal processing unit 351 performs the predetermined signal process on the electrical signal which is obtained from the receiving optical system. This converts the received phosphorescence into the electrical signal corresponding to the oxygen concentration.

Figure 2:
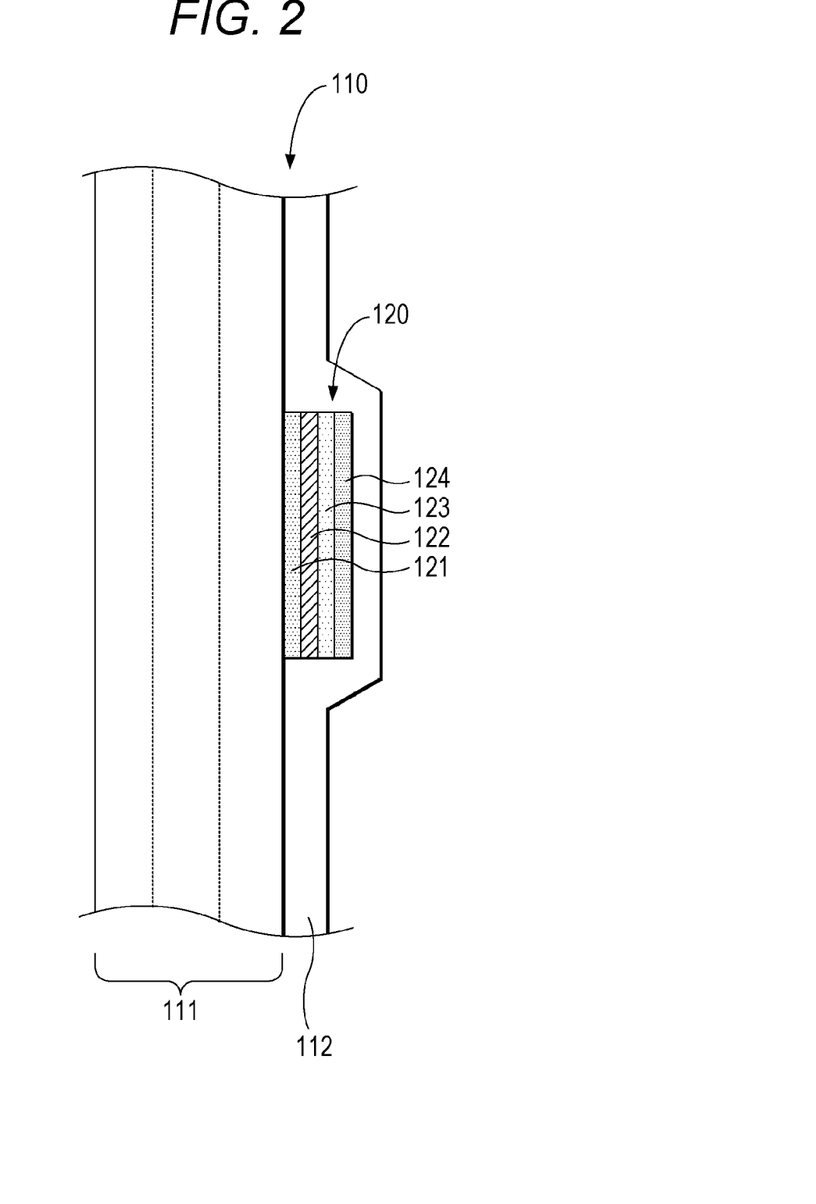
FIG. 2 illustrates an exemplary constitution of the cell culture bag near a sensor chip.

FIG. 2 illustrates an exemplary constitution of the cell culture bag 110 near the sensor chip 120. As described above, the cell culture bag 110 has the multilayer structure. In the multilayer structure, the oxygen permeable film 112 covers the sensor chip 120 arranged on the external film 111. The external film 111 may be the laminated film similar to the conventional cell culture bag 310. For example, the cell culture bag 310 can be constituted so as to be laminated in the order of the ethylene vinyl acetate (EVA) layer, the ethyl vinyl alcohol (EVOH) layer, and the low-density polyethylene (LDPE) layer from the inside. However, another constitution may be employed.

Similar to the conventional sensor chip, the sensor chip 120 includes a reflective film 123 and a light shielding film 124 arranged on one surface of an oxygen-sensitive film 122. The sensor chip 120 is attached to the external film 111 of the cell culture bag 110 with an adhesive layer 121. The adhesive layer 121 is formed at the other surface of the oxygen-sensitive film 122.

The oxygen-sensitive film 122 is a photo-excited substance having, for example, oxygen quenching properties. As such photo-excited substance, the metalloporphyrin complex or a similar complex can be used. The reflective film 123 is used to reflect the excitation light to return this excitation light to the oxygen-sensitive film 122. Thus, the excitation light can be effectively utilized. The light shielding film 124 is used to prevent unwanted external light from entering the optical system 352.

For the oxygen permeable film 112, a film featuring high oxygen permeation rate, good adhesiveness with the external film 111, and a small elution portion is used. As such film, a low-density polyethylene, polytetrafluoroethylene (PTFE), polyurethane, polybutadiene, polydimethylsiloxane, or a similar component is used. However, another material may be employed.

The cell culture bag 110 and the sensor chip 120 of this embodiment are integrally formed. Accordingly, the sensor chip 120 is not exposed to the inside of the cell culture bag 110. Therefore, the user can purchase the sterilized cell culture bag 110 with the sensor chip 120. This eliminates the need for performing additional sterilization treatment. The sensor chip 120 is in contact with the culture fluid 320 via the oxygen permeable film 112. This can prevent a substance contained in the sensor chip 120 from being eluted to the culture fluid 320.

Figure 3:
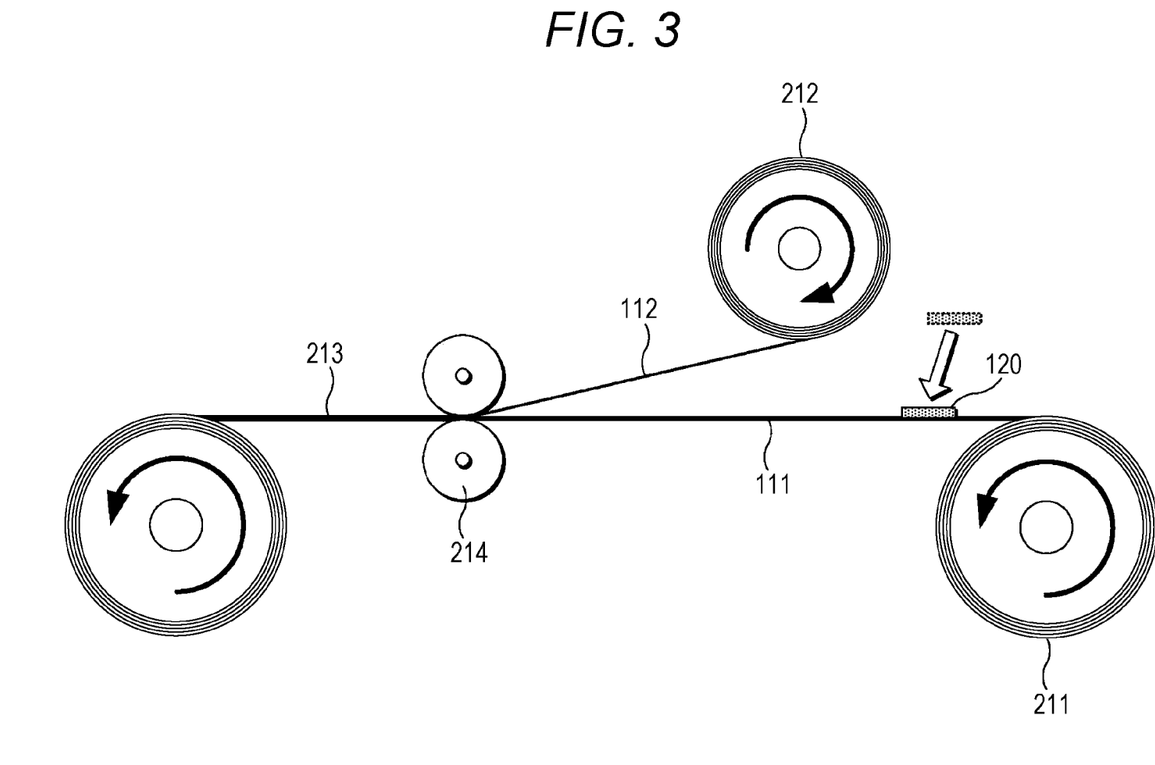
FIG. 3 illustrates an exemplary method for creating a cell culture bag sheet.
Figure 4A:
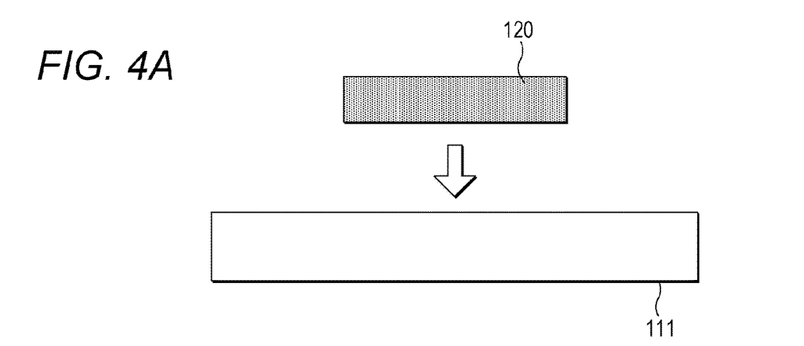
FIGS. 4A to 4D illustrate another exemplary method for creating the cell culture bag sheet.
Figure 4B:
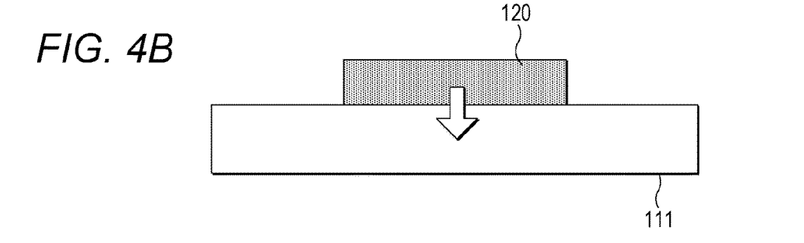
Figure 4C:
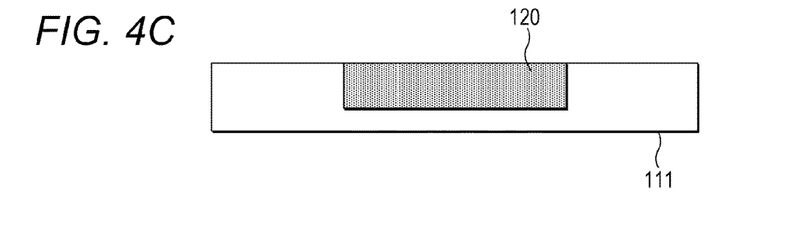
Figure 4D:
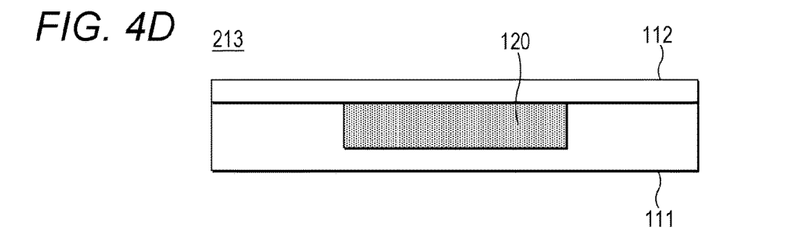

FIG. 3 illustrates an exemplary method for manufacturing the cell culture bag 110 sheet. In the example of this drawing, first, to a roll material 211 of the external film 111, the sensor chip 120 is attached. Next, a roll material 212 of the oxygen permeable film 112 is stacked. Afterwards, performing thermocompression bonding with a thermocompression bonding roll 214 manufactures a sheet 213 of the cell culture bag 110.

Cutting, bonding, or performing a similar operation on this sheet 213 so as to be a predetermined shape, the cell culture bag 110 can be manufactured. However, another manufacturing method may be employed.

For example, as illustrated in FIGS. 4A to 4D, first, the sensor chip 120 may be embedded into the external film 111 by the thermocompression bonding. Next, stacking the oxygen permeable film 112 on the sensor chip 120 can manufacture the sheet 213. In this case, the adhesive layer 121 is unnecessary. This manufacturing method does not generate a difference in level between the external film 111 and the sensor chip 120 at the mounting position of the sensor chip 120. Accordingly, the adhesiveness between the external film 111 and the oxygen permeable film 112 can be enhanced.

Figure 5:
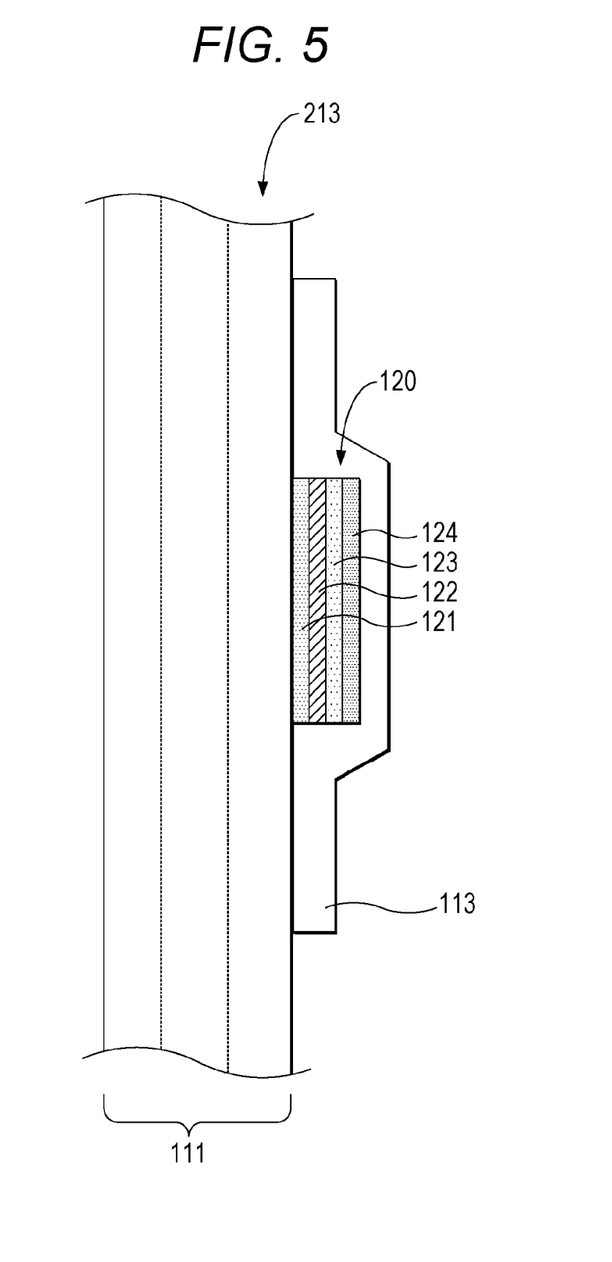
FIG. 5 illustrates another exemplary method for creating the cell culture bag sheet.

In the example of FIG. 5, first, the sensor chip 120 is attached to the external film 111. Next, not to the entire surface of the external film 111, but to a part of a region including the sensor chip 120, an oxygen permeable film 113 is attached to cover the sensor chip 120 by the thermocompression bonding, the adhesive, or a similar method. Thus, the cell culture bag 110 sheet 213 may be manufactured.

Figure 6:
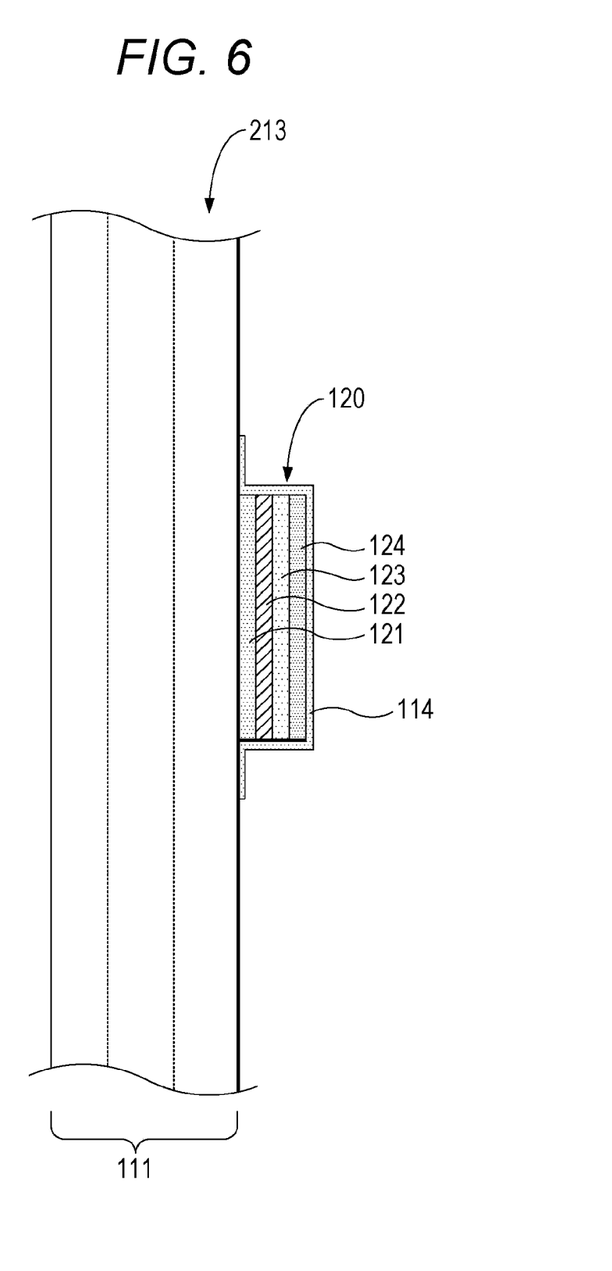
FIG. 6 illustrates another exemplary method for creating the cell culture bag sheet.

Alternatively, as illustrated in FIG. 6, instead of the oxygen permeable film 113, after performing a coating treatment on the sensor chip 120 with a resin 114, the cell culture bag 110 sheet 213 may be manufactured. As the resin 114, a fluororesin, which has high oxygen permeability, or a similar component can be used. Generally, the coating with the resin 114 having high oxygen permeability allows the thickness of the resin 114 to be formed thinner than the oxygen permeable film 113. Accordingly, the coating enhances the oxygen permeability, resulting in improvement of a response speed of the dissolved oxygen concentration measurement.

Figure 7:
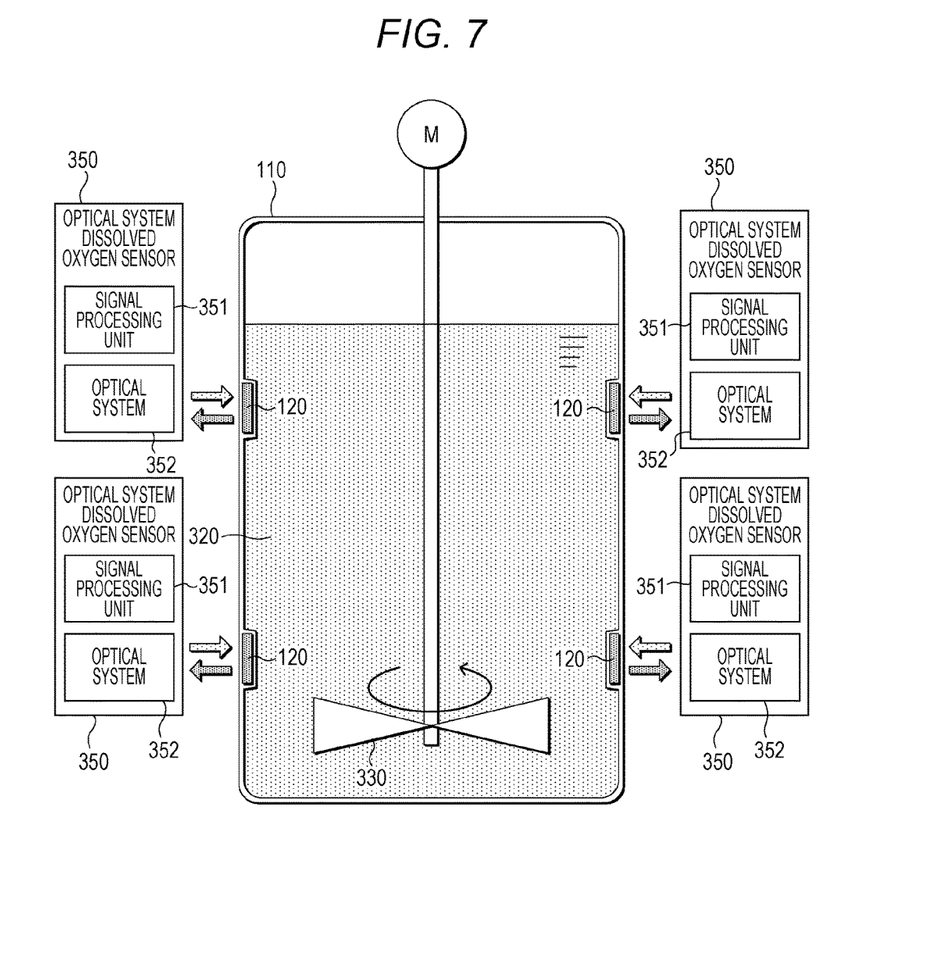
FIG. 7 illustrates an exemplary cell culture bag to which a plurality of sensor chips is mounted.

As illustrated in FIG. 7, the cell culture bag 110 may incorporate the plurality of sensor chips 120. The manufacturing method as exemplified in FIGS. 3 to 6 allows the plurality of sensor chips 120 to be easily incorporated into the cell culture bag 110 without an increase in cost. The use of the plurality of sensor chips 120 allows measuring the dissolved oxygen distribution in the cell culture bag 110. A substance to be detected by each sensor chip 120 may differ.

When incorporating the plurality of sensor chips 120, as illustrated in this drawing, a plurality of optical system dissolved oxygen sensors 350 may be prepared corresponding to the respective sensor chips 120. However, the optical system dissolved oxygen sensor 350 is more expensive than the sensor chip 120. Therefore, using the one optical system dissolved oxygen sensor 350, each sensor chip 120 may be sequentially measured.

Figure 8:
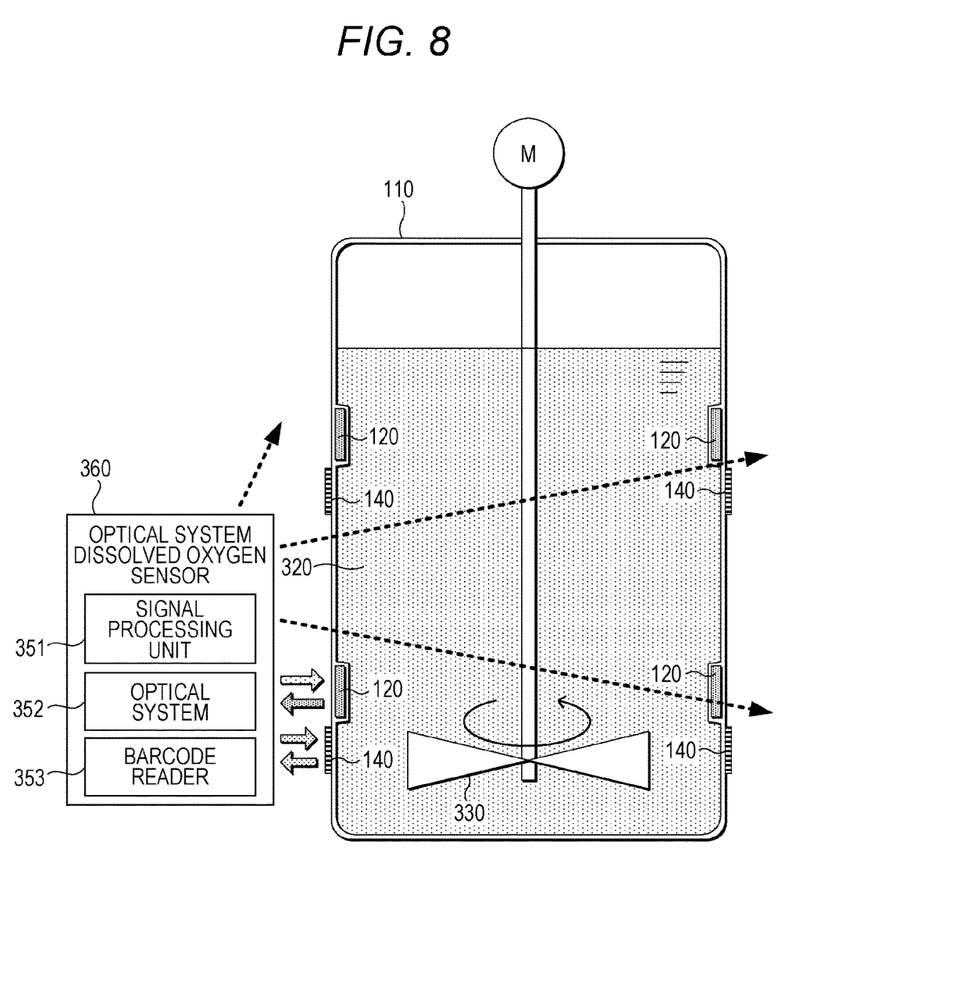
FIG. 8 illustrates another exemplary cell culture bag to which the plurality of sensor chips is mounted.

In this case, as illustrated in FIG. 8, at the proximity of each sensor chip 120 outside of the cell culture bag 110, a barcode 140 may be attached, and an optical system dissolved oxygen sensor 360 may include a barcode reader 353. ID information to identify the sensor chip 120 is written to the barcode 140.

Sequentially measuring each sensor chip 120 using such optical system dissolved oxygen sensor 360 allows reading the barcode 140 simultaneously with the measurement of the phosphorescence from the sensor chip 120. This allows easily making the measured value correspond to the sensor chip 120. Not limited to the barcode 140, by attaching an ID tag or a similar tag to the neighborhood of each sensor chip 120, the optical system dissolved oxygen sensor 360 may be read.

Among the films constituting the sensor chip 120, the oxygen-sensitive film 122, which reacts to the oxygen to be measured, is necessary. However, the reflective film 123 and the light shielding film 124 can be eliminated depending on the situation. The elimination of the reflective film 123 and the light shielding film 124 increases an amount of oxygen permeation from the culture fluid 320 to the oxygen-sensitive film 122. This improves the response speed of the dissolved oxygen concentration measurement.

For example, the reflective film 123 is used to reflect the excitation light to return this excitation light to the oxygen-sensitive film 122. Thus, the excitation light can be effectively utilized. However, in the case where the amount of received phosphorescence is sufficiently obtained, the reflective film 123 may be eliminated. The light shielding film 124 is used to prevent unwanted external light from entering the optical system 352. However, the cell culture bag 110 is often held in a stainless-steel jacket. In this case, since the cell culture bag 110 is insusceptible to the influence of the external light, the light shielding film 124 may be eliminated.

Figure 9:
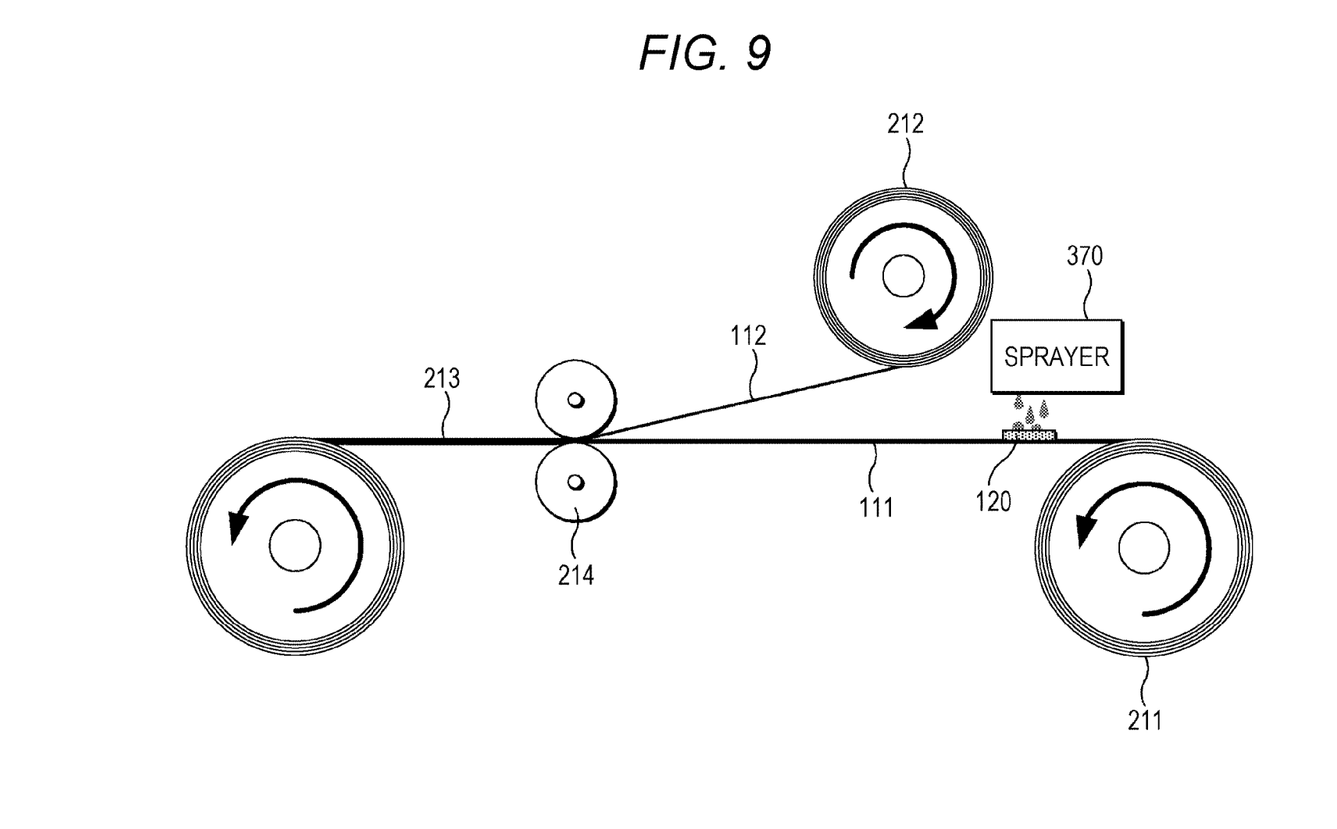
FIG. 9 is an explanatory view in the case where the sensor chip is formed with a sprayer.

To constitute the sensor chip 120 with only the oxygen-sensitive film 122, as illustrated in FIG. 9, first, a powder or liquid oxygen-sensitive material is prepared. Next, by spraying the prepared oxygen-sensitive material from a sprayer 370 to the external film 111, the oxygen-sensitive film 122 may be formed. As the sprayer 370, a sprayer, an ink-jet printer, or a similar component can be used.

Depending on the size and the color of the sensor chip 120, or in the case of the opaque cell culture bag 110 or a similar case, the position of the sensor chip 120 is difficult to be recognized from the outside of the cell culture bag 110. Therefore, arranging the optical system dissolved oxygen sensor 360 at an appropriate position is possibly difficult.

Figure 10A:
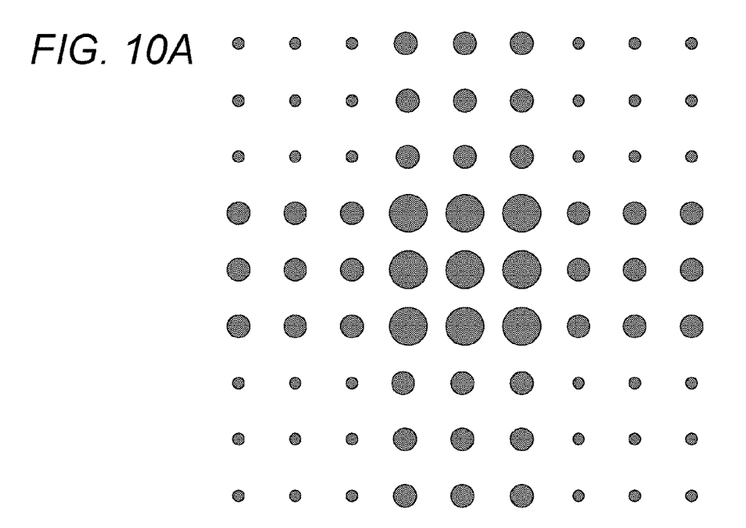
FIGS. 10A and 10B illustrate an exemplary arranged pattern of the sensor chips.

Therefore, for example, in the cell culture bag 110, at the positions shown with the patterns illustrated in FIG. 10A, the plurality of sensor chips 120 may be arranged. In this pattern, the sensor chips included in the center sensor chip group used for the actual measurement have the largest size. The sensor chips included in the sensor chip groups upwardly, downwardly, rightward, and leftward adjacent to the center sensor chip group have the medium size. The sensor chips included in the corner sensor chip groups have the smallest size. This pattern can be easily formed using the sprayer 370.

Figure 10B:
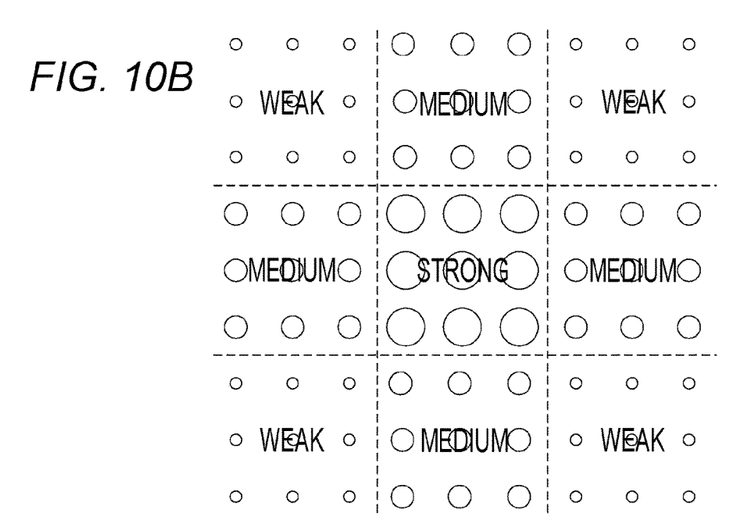

The strength of the phosphorescence that the sensor chip 120 emits corresponds to the size of the sensor chip 120. Therefore, when arranging the sensor chip 120 at the position shown with the pattern as illustrated in FIG. 10A, the optical system dissolved oxygen sensor 360 measures a signal that has the strength as shown in FIG. 10B corresponding to the position.

Therefore, moving the optical system dissolved oxygen sensor 360 in the direction of higher signal strength allows arranging the optical system dissolved oxygen sensor 360 at the appropriate position. Separately from the embodiment, the plurality of sensor chips having the identical size may be arranged at regular intervals. Furthermore, separately from the embodiment, the plurality of sensor chips having the identical size may be regularly arranged at different intervals.

Figure 11:
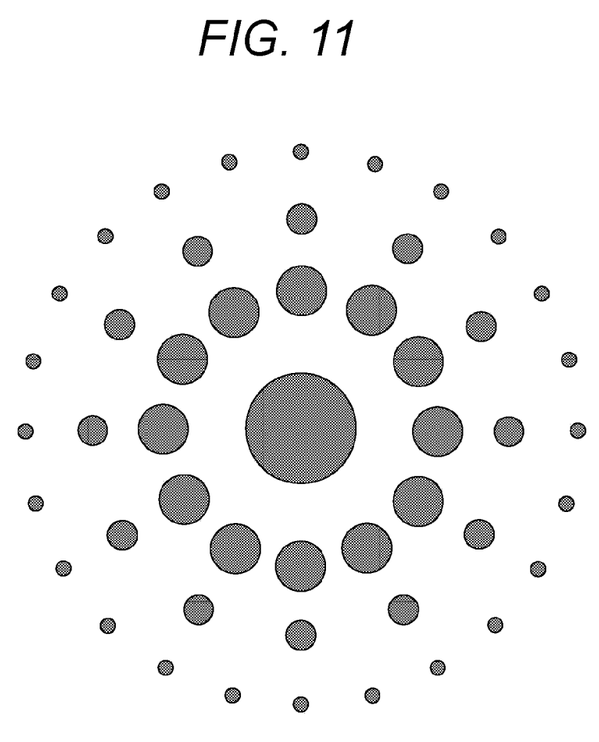
FIG. 11 illustrates another exemplary pattern of the sensor chips.

At the positions shown with the patterns illustrated in FIG. 11, the sensor chips 120 may be arranged. In this pattern, the plurality of sensor chips 120 is concentrically arranged. The sensor chips are arranged such that the sensor chips have a larger size as approaching the center. The use of such pattern also allows arranging the optical system dissolved oxygen sensor 360 at the appropriate position by moving the optical system dissolved oxygen sensor 360 in the direction of higher signal strength.

The cell culture bag of this disclosure is described above with the example of oxygen as the substance to be detected. However, the detection target may be pH, glucose, lactic acid, glutamine, glutamic acid, ammonia, carbon dioxide, or a similar component. In this case, it is only necessary to manufacture the cell culture bag by using the sensor chip reacting to the detection target and covering the sensor chip with the film permeating the object to be detected.

Moreover, the cell culture bag according to an embodiment of this disclosure may be the following first to fourth cell culture bags.

The first cell culture bag houses a culture fluid. The cell culture bag includes: an external film; at least one sensor chip arranged on a culture fluid side of the external film, the at least one sensor chip including a layer reacting to an object to be detected; and a permeable film that covers a culture fluid side of the sensor chip, the permeable film permeating the object to be detected.

The second cell culture bag according to the first cell culture bag includes the permeable film covering an entire inner surface of the external film.

The third cell culture bag according to the first cell culture bag includes the permeable film covering a part of a region including the sensor chip on the inner surface of the external film.

The fourth cell culture bag according to any one of the first to third cell culture bags includes a plurality of the sensor chips arranged. The plurality of the sensor chips is classified into a plurality of sizes. A sensor chip having a largest size is arranged at a center.

A method for manufacturing a cell culture bag according to an embodiment of this disclosure may be a method for manufacturing a cell culture bag for housing a culture fluid. The method may include: attaching at least one sensor chip including a layer reacting to an object to be detected to a roll material that becomes an external film; stacking a roll material that becomes a permeable film to the roll material that becomes the external film to cover the at least one sensor chip, the roll material that becomes the permeable film permeating the object to be detected; and performing thermocompression bonding on both the roll materials.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A cell culture bag comprising:
    an external film;
    at least one sensor chip arranged on an inner surface of the external film, the at least one sensor chip including a layer reacting to an object to be detected, the inner surface being on a culture fluid side of the external film; and
    a permeable film that covers a culture fluid side of the sensor chip, the permeable film permeating the object to be detected,
    wherein the permeable film covers the entire inner surface of the external film,
    wherein the at least one sensor chip comprises a plurality of sensor chips arranged into a plurality of groups,
    wherein a group of sensor chips having the largest size is arranged at the center of the plurality of groups, the remaining groups of sensor chips having a smaller size being arranged around the group of sensor chips having the largest size, and
    wherein the group of sensor chips having the largest size is configured to generate a stronger signal than the remaining groups of sensor chips having a smaller size.

2. The cell culture bag according to claim 1, wherein an arrangement of the group of sensor chips with largest size and the remaining groups of sensor chips having a smaller size aids in positioning an optical system with the group of sensor chips with the largest size, the optical system being located outside of the cell culture bag.

3. A method for manufacturing a cell culture bag comprising:
    attaching a plurality of sensor chips including a layer reacting to an object to be detected to an inner surface of a roll material that becomes an external film, the inner surface being on a culture fluid side of the external film, the plurality of sensor chips being arranged into a plurality of groups;
    stacking a roll material that becomes a permeable film to the roll material that becomes the external film to cover the plurality of sensor chips with the roll material that becomes the permeable film, the roll material that becomes the permeable film permeating the object to be detected, wherein the permeable film covers the entire inner surface of the external film of the cell culture bag; and
    performing thermocompression bonding on both the roll materials, wherein the plurality of sensor chips become embedded into the roll material that becomes the external film, by the performing thermocompression bonding on both the roll materials, wherein a group of sensor chips having the largest size is arranged at the center of the plurality of groups, the remaining groups of sensor chips having a smaller size being arranged around the group of sensor chips having the largest size, wherein the group of sensor chips having the largest size is configured to generate a stronger signal than the remaining groups of sensor chips having the smaller size, and wherein an arrangement of the group of sensor chips with largest size and the remaining groups of sensor chips having the smaller size aids in positioning an optical system with the group of sensor chips with the largest size, the optical system being located outside of the cell culture bag.

4. A method for manufacturing a cell culture bag comprising:

attaching a plurality of sensor chips including a layer reacting to an object to be detected to an inner surface of a roll material that becomes an external film, the inner surface being on a culture fluid side of the external film, the plurality of sensor chips being arranged into a plurality of groups;

stacking a roll material that becomes a permeable film to the roll material that becomes the external film to cover the plurality of sensor chips with the roll material that becomes the permeable film, the roll material that becomes the permeable film permeating the object to be detected, wherein the permeable film covers the entire inner surface of the external film of the cell culture bag; and performing thermocompression bonding on both the roll materials, wherein the plurality of sensor chips become embedded into the roll material that becomes the external film, by the performing thermocompression bonding on both the roll materials, wherein a group of sensor chips having the largest size is arranged at the center of the plurality of groups, the remaining groups of sensor chips having a smaller size being arranged around the group of sensor chips having the largest size, and wherein the group of sensor chips having the largest size is configured to generate a stronger signal than the remaining groups of sensor chips having the smaller size.

* * * * *